United States Patent [19]
Grossi et al.

[11] Patent Number: 5,320,091
[45] Date of Patent: Jun. 14, 1994

[54] CONTINUOUS FLOW HYSTEROSCOPE

[75] Inventors: Benedetto Grossi, Stamford, Conn.; Richard P. Muller, Bronx, N.Y.

[73] Assignee: Circon Corporation, Santa Barbara, Calif.

[21] Appl. No.: 876,068

[22] Filed: Apr. 27, 1992

[51] Int. Cl.$^5$ .............................. A61B 1/00
[52] U.S. Cl. .......................... 128/4; 128/7; 128/6
[58] Field of Search .............. 128/7, 4, 6; 606/46; 604/31, 33

[56] References Cited

U.S. PATENT DOCUMENTS

| | | | |
|---|---|---|---|
| 3,835,842 | 9/1974 | Iglesias | 126/7 |
| 3,850,175 | 11/1974 | Iglesias | 128/7 X |
| 3,939,839 | 2/1976 | Curtiss | 128/7 X |
| 4,132,227 | 1/1979 | Ibe | 128/7 X |
| 4,432,727 | 1/1984 | Windran et al. | 128/7 X |
| 4,630,598 | 12/1986 | Bonnet | 128/7 |

*Primary Examiner*—Richard J. Apley
*Assistant Examiner*—Beverly A. Meindl
*Attorney, Agent, or Firm*—Daniel J. Meaney, Jr.

[57] ABSTRACT

A continuous flow hysteroscope is shown. The hysteroscope includes an outer sheath having an outer surface, an inner surface and a hollowed-out central area extending along a central axis which extends therethrough. The outer sheath has a proximal section and a distal section. The distal end includes a plurality of openings communicating between the outer surface and inner surface. The openings have a predetermined shape and pass fluid exterior to the distal section therethrough and into the hollowed-out central area. The proximal section of the outer sheath includes an outlet and an inlet. An inner member is positioned within the hollowed-out central area and includes a first channel which is adapted to receive a telescope. A second channel, which is substantially parallel to the first channel is utilized for passing a working tool. The first and second channel are operatively coupled to an inlet for passing fluid therethrough and out of the distal end outer sheath. The fluid passageway cooperates with the plurality of openings to pass fluid through the opening from the outer surfaces to the inner surfaces, through the fluid passageway and through the outlet of the outer sheath. The inner member includes an obturator closure means to isolate inflow and outflow distally, to prevent cross flow and to reduce patient trauma at time of insertion of the hysteroscope.

39 Claims, 4 Drawing Sheets

CONTINUOUS FLOW HYSTEROSCOPE

BACKGROUND OF THE INVENTION

1. Field of the Invention

This invention relates to a continuous flow instrument which may be used as a hysteroscope or cystoscope and more particularly relates to a continuous flow hysteroscope having an outer sheath which has a hollowed-out central area which terminates in a distal end and a means for defining an inner member which is located within the hollowed-out central area wherein the means defining the inner member includes means for defining a first channel for receiving a telescope, and a second channel adjacent the first channel for passing a working tool. The outer wall of the first and second channels is spaced from the inner surface of the outer sheath to define a fluid passageway. An obturator closure means is used to isolate fluid flow and to aid in the insertion of the hysteroscope into the uterine cavity to reduce patient trauma. In a procedure, irrigation fluid is passed to the operative site by either one or both of the first channel and second channel to and out of the distal end. Fluid is removed from the operative site by passing the irrigation fluid through a plurality of openings in the distal section of the outer sheath into the fluid passageway to an outlet at the proximal end.

2. Description of the Prior Art

Continuous flow resectoscopes are well known in the art. U.S. Pat. No. 3,835,842 discloses a continuous flow resectoscope for use in urology. Continuous flow resectoscopes have been used for other surgical procedures. An article entitled, *The Use of the Resectoscope in Gynecology*, by Richard A. Auhll, appeared at pages 91 through 99 in the Oct. 11, 1990 issue of the Biomedical Business International (the "Auhll Reference") describes the use of the CIRCON ACMI uterine resectoscope system for gynecological procedures. The Auhll Reference discloses that the use of a continuous flow electrical resectoscope system (CFR) includes a continuous flow irrigation system. Multiple concentric sheaths allow continuous and simultaneous inflow and outflow of non-conducting irrigating solutions so that the surgeon has a clear view through the solution. It is known in the art that the means for passing fluid into the uterus in order to distend the same cannot exceed an intravesical pressure of 90 mm of mercury. If the fluid pressure exceeds 90 mm of mercury, then the fluid is absorbed into the tissue of the uterus which is undesirable in performing an OB-GYN procedure.

In addition, the continuous flow irrigation system provides sufficient flow and pressure to distend and expand the uterus to use the task of the surgeon. Such a system is referred to as a Uterine Resectoscope System. The Uterine Resectoscope System is used for three operative procedures: (i) Myoma resection; (ii) endometrial ablation; and (iii) synechial septo dissection.

The present known continuous flow resectoscope and hysteroscope systems generally pass an irrigating fluid through the center of an inner sheath and out of the distal end to irrigate the operative site. Fluid is removed from the operative site by passing the fluid through a passageway formed between the outer surface of an inner sheath and the inner surface of an outer sheath. Typically, fluid flow is obtained by positioning the source of fluid at a predetermined height in the operating room. For example, positioning a bag of fluid at approximately 1 meter above the operating table will produce 75 mm of mercury head pressure. At a height of 1.4 meter produces approximately 103 mm of mercury pressure at the outlet of the source. The pressure drop through the various tubing and through the resectoscope drops the pressure to a range of 60 mm of mercury to 90 mm of mercury at the distal end of the hysteroscope.

SUMMARY OF THE INVENTION

The present invention discloses a novel, unique and improved hysteroscope which is adapted for use as a continuous flow hysteroscope. In the preferred embodiment, the hysteroscope comprises an outer sheath having an outer surface, an inner surface and a hollowed-out central area extending along a central axis which extends therethrough. The sheath has a proximal section and a distal section. Means are located at the distal section for defining around the outer surface of the sheath a plurality of openings which extend between the outer surface and the inner surface for passing fluid exterior to the distal section through the plurality of openings into the hollowed-out central area. Means are provided for defining at the proximal section of the outer sheath an outlet and an inlet. The hysteroscope further includes means defining an inner member adapted to be positioned within said hollowed-out area wherein the inner member defining means includes means for defining an outer wall located around the periphery of the inner member which is adapted to be spaced from the inner surface of the outer sheath for defining a fluid passageway, a first channel and a second channel. The first channel is adapted to receive a telescope. The second channel, which is substantially parallel to the first channel, is adapted for passing a working tool. The first channel and second channel are operatively connected to an inlet located at the proximal section of the outer sheath for passing fluid through the openings from the outer surface to the inner surface through the fluid passageway and through the outlet of the outer sheath.

In addition, a novel and unique method for performing a surgical procedure using the instrument of the present invention is shown. The method for performing a surgical procedure comprises the step of assembling a continuous flow instrument comprising an outer sheath having an outer surface, and inner surface and a hollowed-out central area wherein the outer sheath has a proximal section having an outlet and an inlet and a distal section having located at pre-selected locations around the outer surface. A plurality of openings which extend between the outer surface and the inner surface for passing fluid exterior to the distal section through the plurality of openings into the hollowed-out central area and means defining an inner member positioned within the hollowed-out central area and wherein the inner member includes means for defining an outer wall located around the periphery of the inner member which is adapted to be spaced from the inner surface of the outer sheath for defining a fluid passageway, a first channel for receiving a telescope and a second channel substantially parallel to the first channel for passing a working tool; and inserting the continuous flow instrument into a cavity.

As described hereinbefore, the prior art continuous flow hysteroscope systems utilize an outer sheath, an inner sheath, a visual obturator for introduction and diagnostic purposes, an operating bridge for operating procedures and additional components in order to perform diagnostic and/or operative procedures. As such, the prior art continuous flow resectoscope/hysteroscope systems having an inner sheath and outer sheath structure do provide a clear visualization of the uterine cavity during diagnostic and operative procedures.

The continuous flow hysteroscope of the present invention overcomes certain of the disadvantages of the prior art systems. One of the advantages of the continuous flow hysteroscope of the present invention is that the inner sheath associated with the prior art systems has been eliminated and replaced by the inner member. As such, the same fluid throughput flow and the size of the accessory or working channel are maintained while reducing the overall outer sheath size to a diameter, in the preferred embodiment, of about 7 mm to about 8 mm. A smaller sheath size is important to the gynecologist since he can minimize dilation of the cervix prior to insertion of the hysteroscope into the uterine cavity.

Another advantage of the present invention is that the continuous flow hysteroscope provides visual atraumatic instrument introduction Another advantage of the present invention that the continuous flow hysteroscope consists of two basic components, an outer sheath and an inner member. In the preferred embodiment, the continuous flow hysteroscope performs three basic functions which include: (i) providing a first channel which is adapted to receive a telescope which functions as a visual obturator; (ii) providing an inner member in the form of an operating bridge having one or two accessory or working channels; and (iii) providing an inflow which passes through one or both of the telescope channel and the accessory or working channels. An obturator closure means is provided to reduce the traumatic effect on a patient during insertion of the hysteroscope and concurrently isolates fluid inflow and outflow.

Another advantage of the present invention is that the inner member utilizes a telescope channel and one accessory or working channel for performing diagnostic procedures. Thereafter, if the surgeon desires to perform an operative procedure requiring an additional accessory channel, the inner member can be easily removed from the outer sheath by means of the first and second connecting means and a second inner member having two working channels can be inserted into the outer sheath and operatively connected to the first connecting means of the outer sheath through a second connecting means. The second inner member includes two accessory or working channels as well as a telescope channel.

Another advantage of the present invention is that the inflow of fluid into the operative site can be provided by means of the telescope channel and/or one or both of the accessory or working channels. Fluid is removed from the operative site by passing the fluid through a plurality of openings which are located at the distal end of the outer sheath and the fluid is passed from the distal end of the outer sheath and through the fluid passageway formed between the outer wall of the inner instrument and the inner wall of the outer sheath. The fluid is then passed from the fluid passageway through an outlet located at the proximal end of the outer sheath.

Another advantage of the present invention is that the continuous flow hysteroscope comprising the outer sheath and means defining the inner member can be used in a hysteroscopy procedure. The method includes the steps of assembling the outer sheath with a means for defining an inner member to form the continuous flow hysteroscope. The means for defining the inner member may be a member having a first channel, used for receiving a telescope, and a second channel for passing a working tool or could include a third channel for passing a working tool.

Another advantage of the present invention is that the method for performing a hysteroscopy procedure can include the step of applying an irrigation fluid to the inlet channel for forming inflow fluid which is directed out of the distal end of the outer sheath and applying a negative pressure to the outlet to urge irrigation fluid external to the distal section through the plurality holes, through the fluid passageway and through the outlet to form a continuous fluid flow at the operative site.

Another advantage of the present invention is that the continuous flow hysteroscope could be used for other procedures such as a cystoscopic procedure, ufologic procedure and the like.

BRIEF DESCRIPTION OF THE DRAWINGS

These and other advantages of the invention will be readily apparent when considered in light of the detailed description hereinafter of the preferred embodiment and of the drawings which include the following figures.

DESCRIPTION OF THE PREFERRED EMBODIMENT

Figure 1:
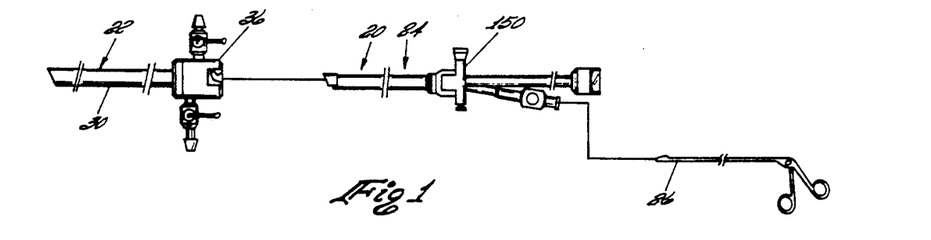
FIG. 1 is a front elevational exploded view of a continuous flow hysteroscope having an outer sheath, an inner member having one working channel and a surgical instrument adapted to pass through the working channel of the inner member.

FIG. 1 illustrates, in an exploded assembly view of the components, an instrument which, in the preferred embodiment, is a continuous flow hysteroscope 20. The basic components of the continuous flow hysteroscope 20 include an outer sheath 22, means defining an inner member or inner instrument 24 and a working tool 26 adapted to be utilized through the working channel of the continuous flow hysteroscope 20. In the preferred embodiment, the working tool is a surgical instrument.

The outer sheath 22 has an outer surface 30 which is operatively connected to a first connecting means 36. The outer sheath 22 extends along a central axis which extends therethrough.

Figure 2:
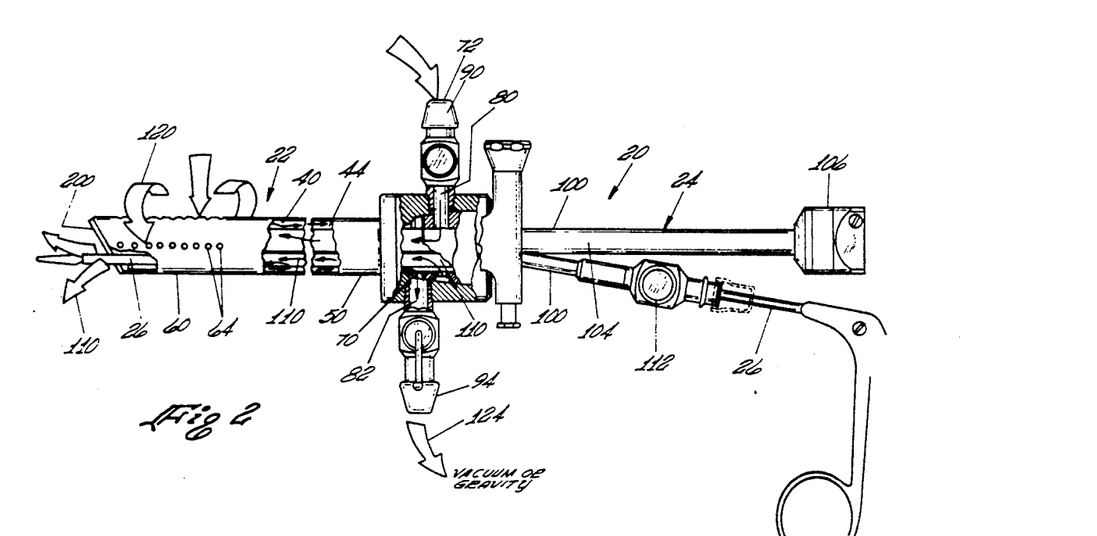
FIG. 2 is a pictorial representation, partially in cross-section, illustrating a continuous flow hysteroscope formed of an outer sheath and an inner member having a first and second connecting means which operatively connects the inner member to the outer sheath and which illustrates pictorially the fluid flow for both the inflow and outflow of fluid through the continuous flow hysteroscope.

FIG. 2 illustrates in greater detail the structure of the outer sheath 22 and the means defining the inner member 24. As illustrated in FIG. 2, the outer sheath 22 has an outer surface 30 which defines the exterior or periphery of the outer sheath 22. The outer sheath 22 further includes an inner surface 40 which defines a hollowed-out central area 44. As illustrated in FIG. 2, the hollowed out central area 44 likewise extends along the central axis of the sheath 22.

As illustrated in FIG. 2, the outer sheath 22 has a proximal section 50 and a distal section 60. The distal section 60 includes means for defining at pre-selected locations around the outer surface 30 a plurality of openings 64 which extend between the outer surface 30 and the inner surface 40. The plurality of openings 64 pass fluid located exterior to the distal section 60 through the plurality of openings and into the hollowed-out central area 44. The proximal end 50 of the outer sheath 22 includes an outlet 70 and an inlet 72.

The first connecting means 36, which is operatively connected to the proximal section 50 of the outer sheath 22, includes means for operatively connecting an inlet channel 80 to the inlet 72 and an outlet channel 82 to the outlet 70, respectively. Inlet channel 80 is operatively connected to a valve member 90, which is, in the preferred embodiment, a stopcock. Outlet channel 82 is operatively connected to valve member 94.

FIG. 2 also illustrates additional details of the means defining an inner member 24. The inner member 24 is adapted to be positioned within the hollowed-out central area 44 of the outer sheath 22. The inner member defining means 24 includes means defining an outer wall 100 which is located around the periphery of the inner member 22. The outer wall 100 is adapted to be spaced from the inner surface 44 of the outer sheath 22. The space between the outer wall 100 of the inner member 24, which is located within the hollowed-out area 44 and the inner surface 40 of the outer sheath 22 defines a fluid passageway therebetween.

The means defining an inner member 24 further includes a first channel 104 which is adapted to receive a telescope 106. In addition, the embodiment of FIG. 2 includes a second channel 108 which operatively is substantially parallel to the first channel 104. The second channel 108 is adapted to pass a working tool. The proximal section of the working channel 108 is positioned to be deflected into communication with an entry port 112 which is adapted to receive a working tool 26.

In the embodiment of FIG. 2, the continuous flow hysteroscope 20 is adapted to be utilized with an outside source of irrigation fluid, such as, for example, a sterilized saline solution, which is utilized for irrigation of the operative site. The irrigation fluid is supplied through the first valve 90 as depicted by arrow 110. The fluid passes through the first valve 90, through the inlet channel 80 and then through both the first channel 104 and second channel 108. The flow direction of the inflow fluid is depicted by arrows 110. As illustrated in FIG. 2 by arrows 110, the fluid flows through both the first channel 104, the second channel 108 and passes out of the orifices of each channel located at the distal end of the distal section 60 as depicted by arrows 110. The irrigation fluid adjacent the operating site being irrigated is then removed from the operative site by applying a small vacuum or negative pressure in the order of about 400 mm Hg. to the outlet valve 94. An alternative is to allow the irrigation to flow out of outlet valve 94 by gravity alone. This results in an outward fluid flow as depicted by arrows 120 located exterior to the outer sheath 22. The fluid passes through the plurality of openings 64 having a predetermined geometrical shape, such as a circular shape, as shown in FIG. 2 and into the fluid passageway which is located in the hollowed-out central area 44 and around the entire outer wall 100 of the inner member 24 and between the inner wall 40 of the outer sheath 22. The outflow depicted by arrows 124 passes through the outlet 70, through the outlet channel 82 and out of the valve member 94 as depicted by arrow 124. The openings 64 are located at preselected locations on the outer sheath distal end 60 adjacent the beak 136 as shown in FIGS. 2 and 3.

Figure 8:
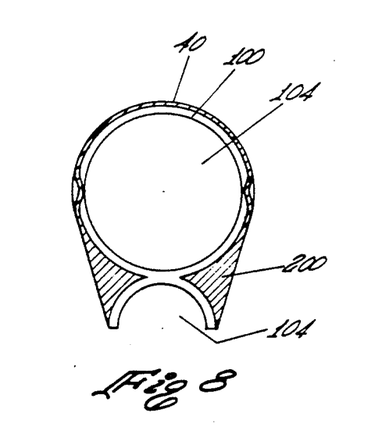
FIG. 8 is a pictorial representation of the obturator closure means for isolating the outlets for inward fluid flow for the telescope channel and a single working channel.

An obturator closure means, shown in detail as element 200 in FIG. 8, is located at distal end of the means defining the inner member 24. The obturator closure means functions to isolate the inlet flow represented by arrows 110 of the distal end 60 of the outer sheath 22 from the outflow fluid shown by arrows 124. In addition, the obturator closure means is shaped to reduce trauma to a patient during insertion of the hysteroscope 20.

Figure 3:
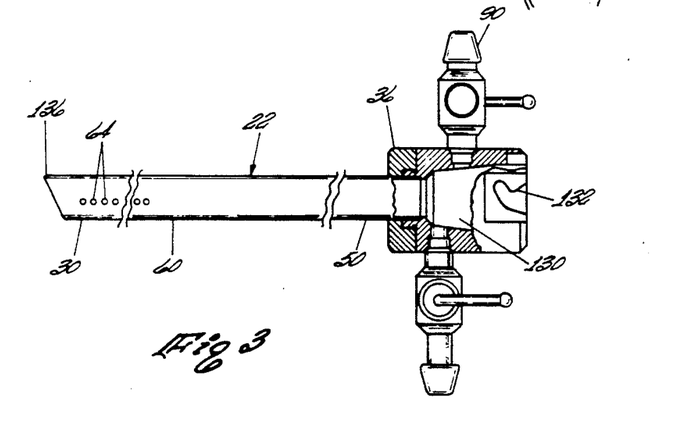
FIG. 3 is a front elevational view, partially in cross-section, showing the structure of the first connecting means operatively connected to the outer sheath which is adapted to be removeably coupled by a second connecting means to an inner member having a telescope channel and a single working channel.
Figure 4:
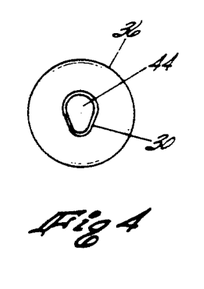
FIG. 4 is a left end elevational view of the outer sheath of FIG. 3.

FIGS. 3 and 4 illustrate the outer sheath 22 as a separate component. The distal end 60 has a plurality of openings 64 formed therein. In the preferred embodiment, the distal section 60 terminates in a beak 136 having a projected end and a recessed end. As illustrated in the embodiment of FIG. 3, the first connecting means 36 is adapted to have a female portion shown as 130 which includes a notched member 132 which is adapted to cooperate with a second connecting means 150 forming part of and operatively coupled to the means defining the inner member 24 which is illustrated in FIG. 2. The second connecting means 150 includes a pin which is adapted to slide into and cooperate with the notched member 132 to form a releasable coupling means to operatively connect the means defining the inner member 24 to the proximal end of the outer sheath 22.

FIG. 4 illustrates the left side view of the outer sheath 22 showing that the hollowed-out central area 44 is tear drop shaped in the preferred embodiment.

Figure 5:
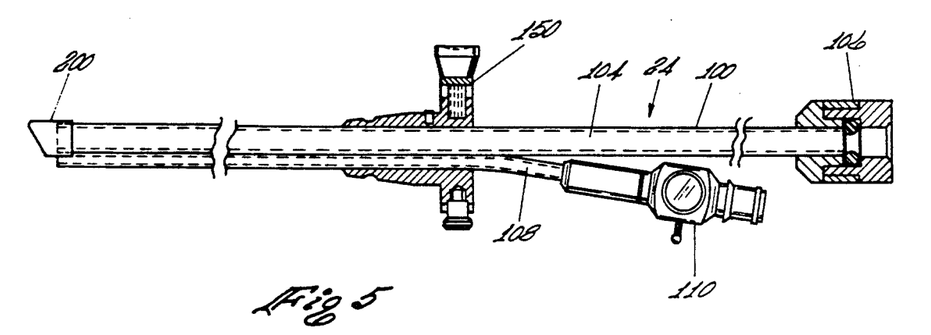
FIG. 5 is a partial cross-sectional view of an inner member having a second connecting means, a telescope channel and a single working channel.

FIG. 5 shows in greater detail the structure of the means defining the inner member 24 having a telescope channel and a single working channel. As illustrated in FIG. 5, the first channel 104 and the second channel 108 extend substantially parallel to each other in that portion of the inner member 24 which is adapted to be positioned within the hollowed-out central area of the outer sheath. The distal end of the inner member 24 has a cooperating obturator closure means 200 which is adapted to slidably engage the inner surface of the outer sheath 22.

Figure 6:
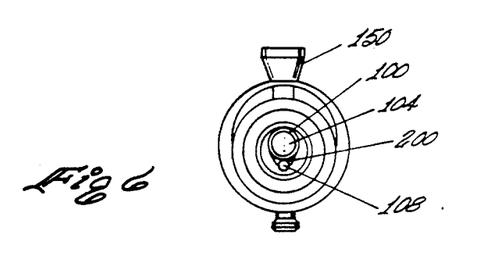
FIG. 6 is a left end elevational view of the inner member of FIG. 5.
Figure 7:
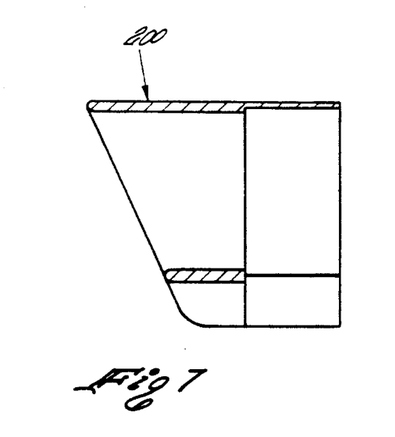
FIG. 7 is a cross-sectional elevational view of the distal end of the outer sheath wherein the distal end has a shield and an obturator closure means.

FIG. 6 shows on the left end elevational view the structural relationship between the first channel 104, the second channel 108 and the obturator closure means 200. The second connecting means 150 is shown to have a thumb contacting means which is utilized to urge positive disengagement of the coupling means to separate the inner member 24 from the outer sheath 22. The first connecting means 36 and second connecting means 150 are the preferred embodiment for practicing this invention. It is envisioned that other known connecting means, such as, for example, a bayonet connecting means could be used for practicing this invention FIG. 7 illustrates, in greater detail, the structure of shield 160 and the obturator closure means 200.

FIG. 8 illustrates the geometrical shape of the obturator closure means which surrounds and shields the first channel 104 and the second channel 108 with the inner surface 40 of the outer sheath 22

FIGS. 9 through 17 utilize similar components, such as the outer sheath 22, the first connecting means 36, the means defining the inner member 24, the second connecting means 150, the surgical working tool 26 and the like. Thus, FIGS. 9 through 17 utilize similar numbers for similar components as utilized in the description of FIGS. 1 through 8, and will not be repeated herein.

Figure 9:
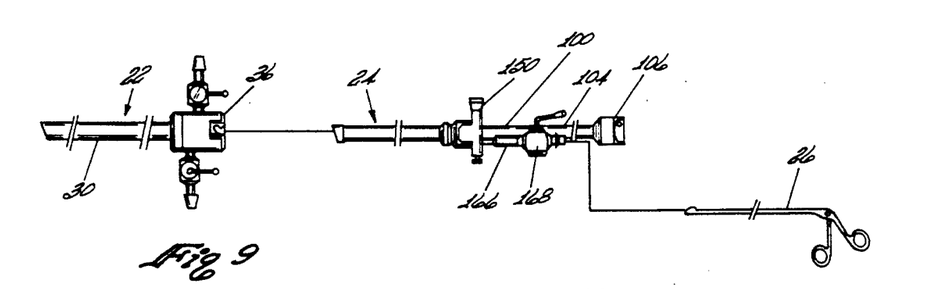
FIG. 9 is a front elevational exploded view of a continuous flow hysteroscope having an outer sheath, an inner member having a telescope channel and two working channels and a surgical instrument which is adapted to be passed through one of the working channels.

In FIG. 9, the means defining the inner member 24 includes a telescope channel 104 and two working channels or accessory channels 160 and 166. In addition, the telescope channel 104 extends along the central axis of the means defining the inner member 24 in a manner similar to that of FIG. 1. However, the means defining the inner member 24 in FIG. 9 utilizes two working channels. In the embodiment illustrated in FIG. 9, the axis of each of the working channels 160 and 166 is substantially parallel to the axis of the means defining the inner member 24 and the axis of the first channel 104 which is adapted to receive the telescope.

In the single working channel embodiment illustrated in FIG. 1, the proximal end of the working channel is deflected relative to the axis of the telescope channel for passing the single working tool.

Figures 10, 11, 12, 13:
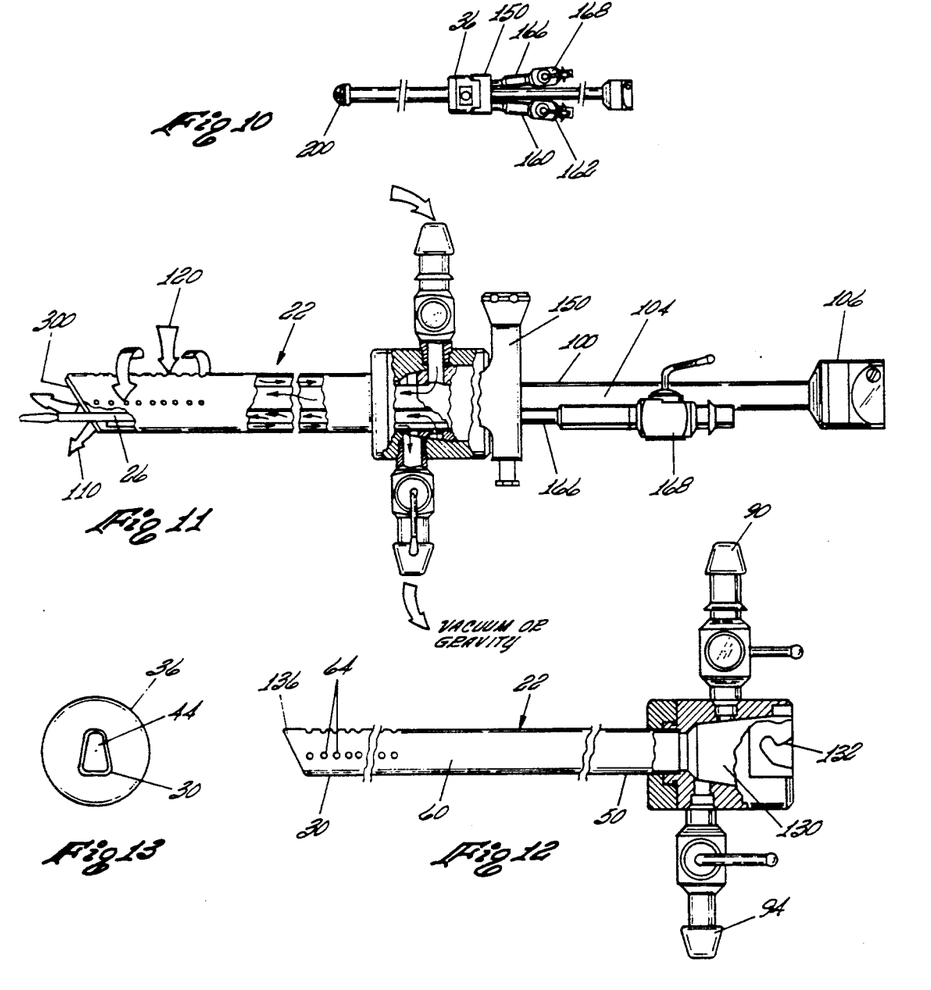
FIG. 10 is a partial top view of an inner member of FIG. 9 having a telescope channel having a telescope located therein and two working channels having an entry part operatively connected to each of the working channels.
FIG. 11 is a front elevational view partially in cross-section showing the continuous flow hysteroscope having an outer sheath and the inner member with a telescope channel and two working channels.
FIG. 12 is a partial front elevational partially in cross-section showing a first connecting means operatively connected to the outer sheath which is adapted to receive and cooperate with a second connecting means operatively connected to an inner member having a telescope channel and two working channels.
FIG. 13 is a left end elevational view of the outer sheath of FIG. 12.

FIG. 10 is a partial pictorial bottom view showing a fully assembled continuous flow hysteroscope having an inner member 24 which has a first channel 104 for receiving a telescope 106 and two working channels 160 and 166. Working channel 160 is operatively connected to an entry port 162 while the second working channel 166 is operatively connected to a second operative port 168.

FIG. 11 illustrates the fluid flow pattern for the means defining inner member 24 having a telescope channel and two working channels. The fluid flow is similar to that as described in connection with FIG. 2 hereof. As illustrated in FIG. 11, the axis of the working channel 166 is substantially parallel to the axis of the telescope channel 104. The working channel 166 extends axially throughout the length of the means defining the inner member 24 and through the hollowed-out central area of the outer sheath 22.

FIG. 12 shows that the structure of the outer sheath 22 for use with a means defining an inner member 24 having a telescope channel and two working channels has substantially the same structure as that utilized for a means defining an inner member 24 having a telescope channel and a single working channel. The difference is that the structure of the means defining the inner member 24 is viewed from the left side, which is depicted in FIG. 13, differs from that of FIG. 4. The difference is that the distal end of the means defining the inner member 24 is substantially triangular shaped so as to position the first channel at the top of the triangle and each of the working channels is in a parallel position located at the base of the triangle. This is illustrated in greater detail in FIG. 16.

Figure 14:
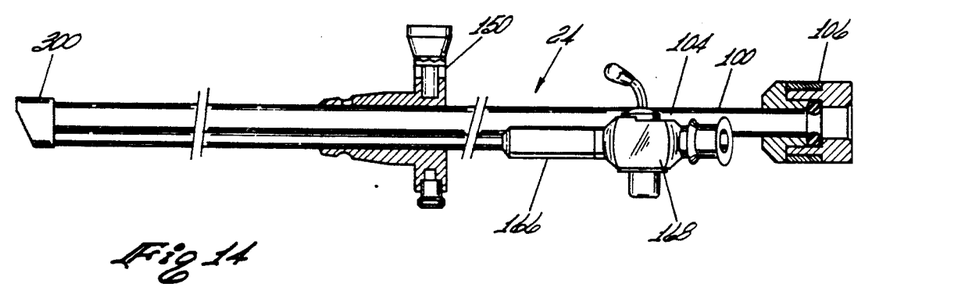
FIG. 14 is a partial cross-sectional view of an inner member having a second connecting means, telescope channel and two working channels.

FIG. 14 illustrates the obturator closure means 300 as well as the relationship between the working channel 166 and the entry port 168.

Figure 15:
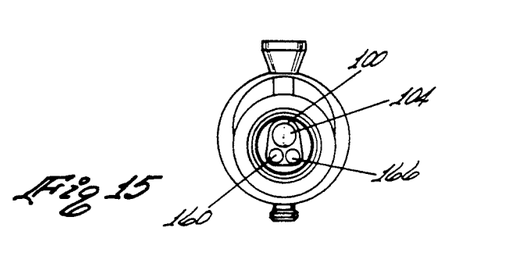
FIG. 15 is a left end elevational view of the inner member of FIG. 14.

FIG. 15 shows, in the left end view, the substantially triangular cross-section of the distal end of the means defining the inner member 24 and shows that the first channel 104 is substantially larger than and is positioned on top of each of the working channels 160 and 166. The obturator closure means 300 isolates the orifice of each of the channels 104, 160 and 166 so as to isolate the inflow from the outflow. The obturator closure means 300 is also shaped in a desired shape to reduce patient trauma during insertion of the continuous flow hysteroscope.

Figure 16:
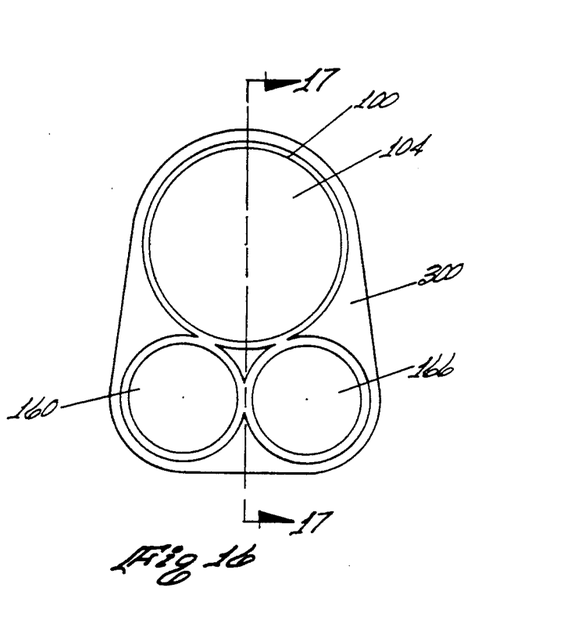
FIG. 16 is a left end elevational view of the distal end of the inner member having a telescope channel and two working channels.

FIG. 16 shows in greater detail the structure of the distal end of the means defining the inner member 24. As illustrated in FIG. 16, the first channel 104 which is adapted to receive the telescope is positioned on top of each of the working channels 160 and 166. The inflow of fluid can be accomplished by passing fluid through any one of the first channel 104, the second channel 160, which is one working channel and a third channel 166 which is another working channel. Also, the obturator closure means 300 is shown to isolate the orifice from each of the channels 104, 160 and 166 to insure that the inward flow of fluid is directed to the operative site.

Figure 17:
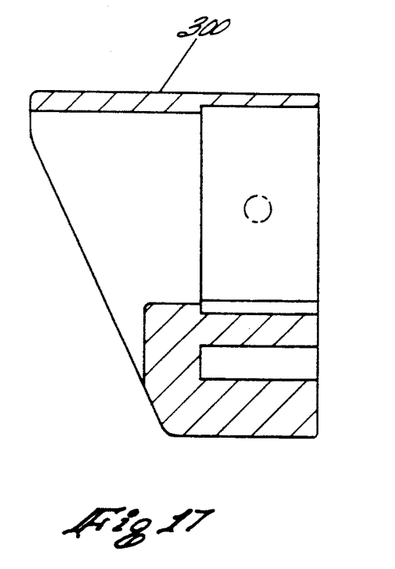
FIG. 17 is a sectional view taken along section lines 17—17 of FIG. 16 showing that the shape of the shield forming the distal end of the inner member of FIG. 14.

FIG. 17 illustrates, in cross-section, the structure of the obturator closure means 300 located in the distal end of the means defining the inner member 24. Also, the location of the obturator closure means 300 is depicted in FIG. 17.

The continuous flow hysteroscope of the present invention is capable of providing sufficient flow and pressure to distend and expand the uterus to enable a surgeon to conduct both diagnostic and operative procedures. During usage, the surgeon would typically assemble an outer sheath with an inner member having the desired telescope channel and number of working channels.

Depending on the requirements of a surgical procedure, whether a diagnostic or therapeutic procedure, a surgeon can utilize an inner member having a telescope channel and one working channel which is operatively connected to the outer sheath to form the continuous flow hysteroscope which is a dedicated instrument. However, if the surgeon requires two working tools to perform a procedure, a separate dedicated continuous flow hysteroscope having an inner member having two working channels can be used. Thus, during insertion, the telescope provides the surgeon with the ability to have visualization during insertion. The shape of the obturator closure means enables the surgeon to make the insertion with reduced trauma to a patient. Once the continuous flow hysteroscope has been placed into the uterus, the surgeon then can commence the irrigation flow to give clear visualization for performing the diagnostic and operative procedures.

What is claimed is:

1. An instrument comprising
an outer sheath having an outer surface and a hollowed-out central area extending along a central axis which extends therethrough, said outer sheath having a proximal section and a distal section having a plurality of openings which extend between the outer surface and the hollowed-out central area;
means defining an inner member positioned within said hollowed-out central area and forming a fluid passageway between the outer sheath and inner member, said inner member defining means including means for defining
a first channel for receiving a telescope;
a second channel substantially parallel to said first channel for passing a working tool; and
obturator closure means located at said distal end for sealing around the inner member that position of the fluid passageway located between the inner member and the outer sheath to isolate fluid inflow through the first channel and second channel from fluid outflow passing through said fluid passageway, said obturator closure means being shaped to reduce trauma during insertion of the instrument into a cavity during a procedure;
said inner member cooperating with said first and second channels to pass fluid through said distal end and said fluid passageway cooperating with said plurality of openings to pass fluid through said openings from the outer surface, through the fluid passageway and through the proximal section of the outer sheath.

2. The instrument of claim 1 wherein said openings have a predetermined geometrical shape.

3. The instrument of claim 2 wherein the predetermined geometrical shape of the openings is circular.

4. The instrument of claim 1 wherein said means defining said inner member further includes
a third channel substantially parallel to said first channel and said second channel for passing a second working tool.

5. The instrument of claim 1 wherein said inner member defining means including means for defining an inlet which is operatively coupled to at least one of said first channel and said second channel and an outlet which is operatively coupled to said fluid passageway.

6. The instrument of claim 1 wherein said inner member defining means further includes means for defining an inlet which is operatively coupled to each of said first channel and said second channel.

7. The instrument of claim 4 wherein said inner member defining means includes means for defining an inlet which is operatively connected to at least one of said first channel, said second channel and said third channel.

8. The instrument of claim 7 wherein said inner member defining mean further includes means for defining an inlet which is operatively coupled to each of said first channel, said second channel and said third channel.

9. The instrument of claim 5 wherein said outer sheath includes
a first connecting means located at the proximal section of said outer sheath, said first connecting means including
means defining an inlet channel which communicates with said inlet for passing fluid from the connecting means through the inlet to at least one of said first channel and said second channel; and
means defining an outlet channel which communicates with said outlet for passing fluid from said fluid passageway through the outlet channel.

10. The instrument of claim 1 wherein said
obturator closure means is triangularly shaped to reduce trauma during insertion of the instrument into a cavity during a procedure.

11. The instrument of claim 9 wherein said mean defining said inner member further includes
a second connecting means which is removeably connected to said first connecting means of said outer sheath for coupling said outer sheath to said inner member when said inner member is positioned within the hollowed-out central area of said outer sheath.

12. A continuous flow hysteroscope comprising
an outer sheath having an outer surface, an inner surface and a hollowed-out central area extending along a central axis which extends therethrough, said outer sheath having a proximal section and a distal section;
means located at said distal section for defining a beak which communicates with said hollowed-out central area, said distal section including means defining at pre-selected locations around the periphery thereof a plurality of openings having a predetermined geometrical shape for passing fluid exterior to the beak and distal section through the openings and into said hollowed-out central area;
means defining at said proximal section of the outer sheath an inlet and an outlet;
means defining an inner member adapted to be positioned within said hollowed out central area, said inner member defining means including means for defining:
an outer wall located around the periphery of said inner member which is adapted to be spaced from the inner surface of said outer sheath for defining a fluid passageway;

a first channel for receiving a telescope;

a second channel substantially parallel to said first channel for passing a working tool;

obturator closure means located at said distal end for sealing around the inner member that position of the fluid passageway located between the inner member and the outer sheath to isolate fluid inflow through the first channel and second channel from fluid outflow passing through said fluid passageway, said obturator closure means being shaped to reduce trauma during insertion of the instrument into a cavity during a procedure;

said first and second channel being operatively coupled to said inlet for passing fluid through said obturator and out of said outer heath through the beak, said fluid passageway cooperating with said plurality of openings to pass fluid through the openings located in said distal section, through the fluid passageway and through the outlet of the outer sheath.

13. The continuous flow hysteroscope of claim 12 further comprising a first connecting means located at the proximal section of said outer sheath.

14. The continuous flow hysteroscope of claim 13 wherein the predetermined shape of the openings is circular.

15. The continuous flow hysteroscope of claim 12 wherein said means defining said inner member further includes a third channel substantially parallel to said first channel and said second channel for passing a second working tool.

16. The continuous flow hysteroscope of claim 15 wherein said inner member defining means includes means for defining an inlet which is operatively connected to at least one of said first channel, said second channel and said third channel.

17. The continuous flow hysteroscope of claim 15 wherein said inner member defining means further includes means for defining an inlet which is operatively coupled to each of said first channel, said second channel and said third channel.

18. The continuous flow hysteroscope of claim 12 wherein said outer sheath includes a first connecting means located at the proximal section of said outer sheath, said first connecting means including means defining an inlet channel which communicates with said inlet for passing fluid from the first connecting means through the inlet to at least one of said first channel and said second channel; and means defining an outlet channel which communicates with said outlet for passing fluid from said passageway through the outlet channel.

19. The continuous flow hysteroscope of claim 12 wherein said obturator closure means is triangularly shaped to reduce trauma during insertion of the hysteroscope during a hysteroscopy procedure.

20. The continuous flow hysteroscope of claim 19 wherein said means defining said inner member further includes a second connecting means which is adapted to be removeably connected to said first connecting means of said outer sheath for coupling said inner member, to said outer sheath when said inner member is positioned within the hollowed-out central area of said outer sheath.

21. The continuous flow hysteroscope of claim 19 further comprising a telescope located in said first channel which cooperates with said obturator closure means to form a visual obturator.

22. A method for performing a medical procedure comprising the steps of assembling an instrument comprising an outer sheath having an outer surface and a hollowed-out central area wherein the outer sheath has a proximal section and a distal section having a plurality of openings which extend between the outer surface and the hollowed-out central area for passing fluid exterior to the distal section through the plurality of openings into the hollowed-out central area and a means defining an inner member positioned within said hollowed-out central area and forming a passageway between the outer sheath and inner member and wherein the inner member includes means for defining a fluid passageway, a first channel for receiving a telescope and a second channel substantially parallel to the first channel for passing a working tool and an obturator closure means separating fluid in flow from fluid outflow; and inserting the instrument into a cavity.

23. The method of claim 22 further comprising the step of applying an irrigation fluid to an inlet located at the proximal section of said outer sheath and operatively coupled to at least one of the first channel and the second channel and passing the irrigation fluid through at least one of the first channel and the second channel and out of the distal end of the outer sheath.

24. The method of claim 23 further comprising the step of applying a negative pressure to an outlet located at the proximal end of the outer sheath and operatively coupled to a fluid passageway to urge irrigation fluid located exterior to the distal section of the outer sheath through the plurality of openings from the outer surface, through the fluid passageway and through the outlet of the outer sheath.

25. The method of claim 23 further comprising the step of placing a telescope into the first channel prior to the step of inserting the instrument into the cavity to provide visualization to a surgeon during insertion.

26. The method of claim 24 further comprising the step of performing a surgical procedure by passing a working tool through the second channel.

27. The method of claim 23 wherein the means defining the inner member of the instrument further includes a third channel capable of passing a working tool and wherein the method further comprising the step of performing a procedure utilizing the third channel.

28. The method of claim 27 wherein the step of performing a procedure utilizing the third channel includes the step of passing a working tool through the third channel.

29. The method of claim 27 wherein the inlet is operatively coupled to the third channel further comprising the step of applying an irrigation fluid to the inlet and passing irrigation fluid through at least one of the first channel, the second channel and the third channel.

30. The method of claim 27 wherein the inlet is operatively coupled to the third channel further comprising the step of applying an irrigation fluid to the inlet and passing irrigation fluid through each of the first channel, the second channel and the third channel.

31. A method for performing a hysteroscopy procedure comprising the steps of assembling a continuous flow hysteroscope comprising an outer sheath having an outer surface, an inner surface and a hollowed-out central area wherein the outer sheath has a proximal section having an outlet and an inlet and a distal section having located at pre-selected locations around the outer surface a plurality of openings which extend between the outer surface and the inner surface for passing fluid exterior to the distal section through the plurality of openings into the hollowed-out central area and a means defining an inner member positioned within said hollowed-out central area and wherein the inner member includes means for defining an outer wall located around the periphery of the inner member which is adapted to be spaced from the inner surface of the outer sheath for defining a fluid passageway, a first channel for receiving a telescope and a second channel substantially parallel to the first channel for passing a working tool and an obturator closure means separating fluid in flow from fluid outflow; and inserting the continuous flow hysteroscope into a uterine cavity.

32. The method of claim 31 further comprising the step of applying an irrigation fluid to the inlet and passing the irrigation fluid through at least one of the first channel and the second channel and out of the distal end of the outer sheath.

33. The method of claim 32 further comprising the step of applying a negative pressure to the outlet to urge irrigation fluid located exterior to the distal section of the outer sheath through the plurality of openings from the outer surface to the inner surface, through the fluid passageway and through the outlet of the outer sheath.

34. The method of claim 32 further comprising the step of placing a telescope into the first channel prior to the step of inserting the continuous flow hysteroscope into the uterine cavity to provide visualization to a surgeon during insertion.

35. The method of claim 33 further comprising the step of performing a surgical procedure on a patient by passing a working tool through the second channel.

36. The method of claim 32 wherein the means defining the inner member of the continuous flow hysteroscope further includes a third channel capable of passing a working tool and wherein the method further comprising the step of performing a surgical procedure on a patient utilizing the third channel.

37. The method of claim 36 wherein the step of performing a surgical procedure utilizing the third channel includes the step of passing a working tool through the third channel.

38. The method of claim 36 wherein the inlet is operatively coupled to the third channel further comprising the step of applying an irrigation fluid to the inlet and passing irrigation fluid through at least one of the first channel, the second channel and the third channel.

39. The method of claim 36 wherein the inlet is operatively coupled to the third channel further comprising the step of applying an irrigation fluid to the inlet and passing irrigation fluid through each of the first channel, the second channel and the third channel.

* * * * *